United States Patent [19]

Neumann et al.

[11] Patent Number: 5,086,760
[45] Date of Patent: Feb. 11, 1992

[54] ARTICULATED ORTHOTIC BRACE FOR AN ANATOMICAL JOINT

[76] Inventors: Holm W. Neumann, 803 NW. Tyler, Corvallis, Oreg. 97330; Thomas J. Maddock, 45937 McKenzie Hwy., Vida, Oreg. 97488

[21] Appl. No.: 715,735

[22] Filed: Jun. 17, 1991

Related U.S. Application Data

[63] Continuation of Ser. No. 338,737, Apr. 14, 1989, abandoned.

[51] Int. Cl.⁵ .................................................. A61F 5/00
[52] U.S. Cl. .................................................. 602/27; 602/6
[58] Field of Search ............ 128/80 R, 80 H, 80 F, 128/80 J, 166, 88

[56] References Cited

U.S. PATENT DOCUMENTS

| 621,366 | 3/1899 | Olsen | 128/88 |
|---|---|---|---|
| 1,336,001 | 4/1920 | Tranmer | 128/80 H |
| 1,381,290 | 6/1921 | Diadul | 128/80 J |
| 1,885,448 | 11/1932 | Jones | 128/85 |
| 3,799,158 | 3/1974 | Gardner | 128/80 C |
| 3,970,083 | 7/1976 | Carrigan | 128/166 |
| 4,428,369 | 1/1984 | Peckham et al. | 128/80 C |
| 4,463,751 | 8/1984 | Bledsoe | 128/88 |
| 4,523,585 | 6/1985 | Lamb | 128/80 C |
| 4,531,731 | 7/1985 | Law | 128/80 C |
| 4,574,790 | 3/1986 | Wellershaus | 128/78 |
| 4,614,181 | 9/1986 | Karlsson | 128/80 C |
| 4,620,532 | 11/1986 | Houswerth | 128/80 C |
| 4,665,904 | 5/1987 | Lerman | 128/80 H |
| 4,723,539 | 2/1988 | Townsend | 128/80 C |
| 4,738,252 | 4/1988 | Friddle et al. | 128/80 C |
| 4,881,532 | 11/1989 | Borig et al. | 128/80 F X |
| 4,922,630 | 5/1990 | Robinson | 128/80 H |
| 4,934,355 | 6/1990 | Porcelli | 128/80 H |

FOREIGN PATENT DOCUMENTS

| 8502536 | 6/1985 | PCT Int'l Appl. | 128/80 F |
|---|---|---|---|
| 8804542 | 6/1988 | PCT Int'l Appl. | 128/80 C |

Primary Examiner—Edgar S. Burr
Assistant Examiner—Moshe I. Cohen
Attorney, Agent, or Firm—Kolisch, Hartwell, Dickinson, McCormack & Heuser

[57] ABSTRACT

An articulated, orthotic brace for providing support to an anatomical joint including a first support for detachably engaging a body portion adjacent the joint, a second support for detachably engaging a body portion on the opposite side of the joint, and an articulated device interconnecting the first and second supports defined by first and second articular members selectively movable relative to one another and adjustable over a predetermined range to approximate anatomical motion of the joint.

18 Claims, 2 Drawing Sheets

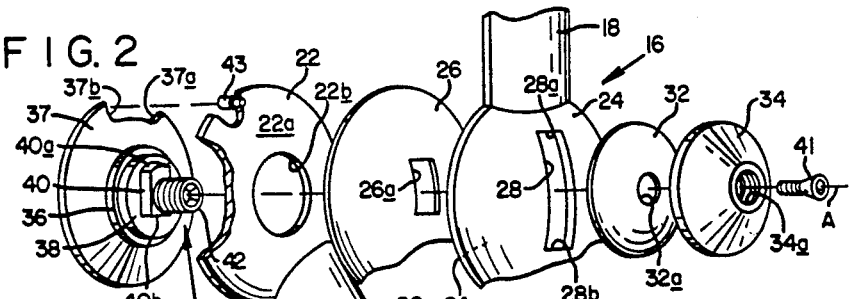

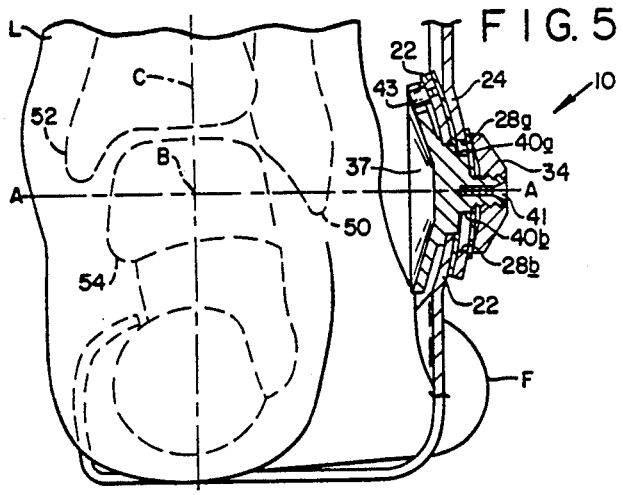
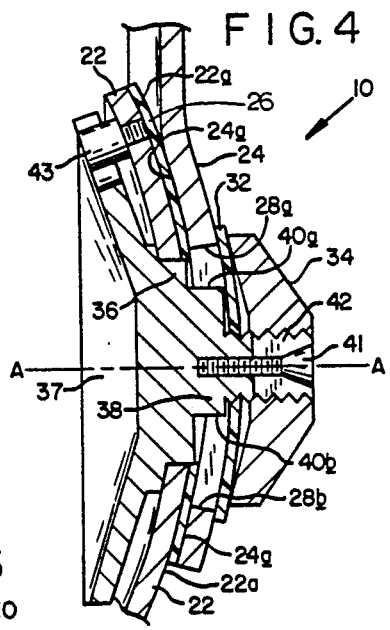
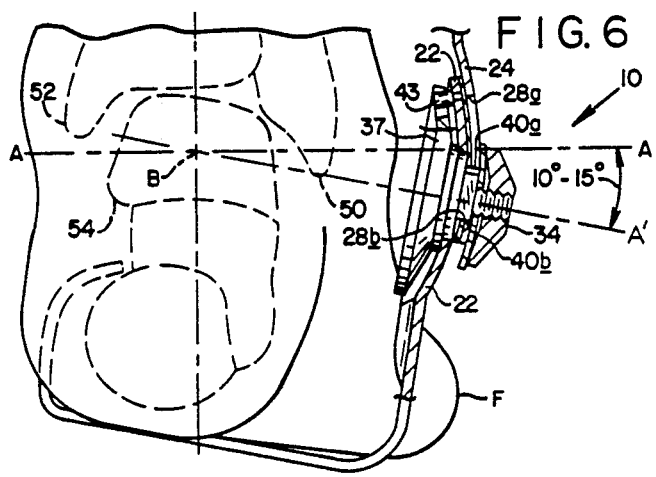
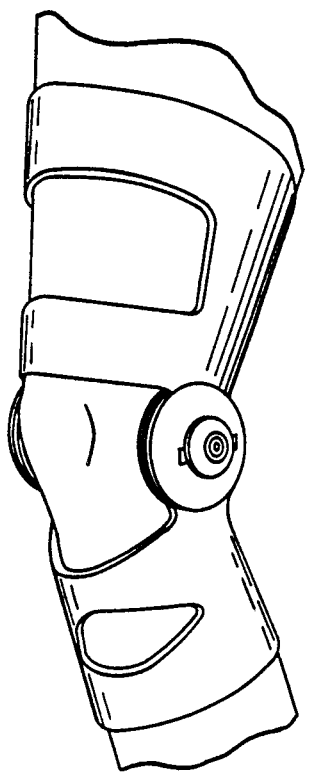
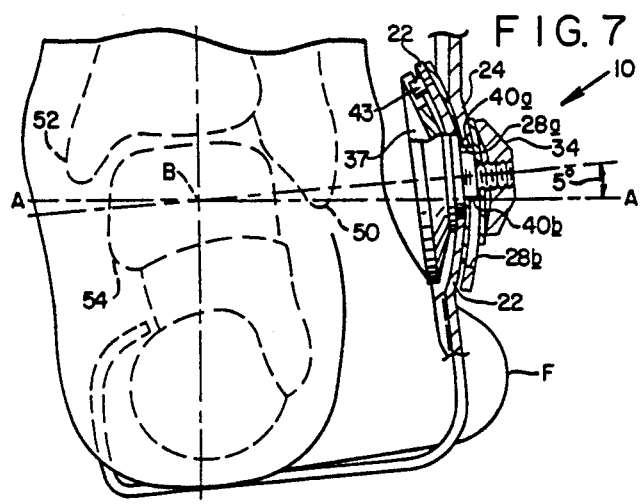

ARTICULATED ORTHOTIC BRACE FOR AN ANATOMICAL JOINT

This application is a continuation of application Ser. No. 07/338,737, filed Apr. 14, 1989, abandoned with the filing of this continuation application.

BACKGROUND AND SUMMARY OF THE INVENTION

The present invention relates to orthopedics and orthodontics, and more particularly to a novel orthotic brace for providing protection, support/stabilization and rehabilitation of an injured anatomical joint. Alternatively, the orthotic brace can be used as a device to prevent injury to a joint. The orthotic brace is constructed with a novel, articulated mechanical device which, when the brace is in position, permits the joint to move through selected, limited ranges corresponding to its normal anatomical motion. The orthotic brace of the present invention may be used on virtually all major anatomical joints, such as the ankle, knee, hip, elbow, wrist, shoulder, etc. For purposes of explanation, however, discussion will be limited principally to application of the orthotic brace to the ankle joint.

The ankle joint is a complex mechanism, and its motion is a remarkable example of the intricate interplay of bone and ligaments and their protective action upon one another. The ankle may be thought of as a hinge joint, although that may be somewhat of an oversimplification. Essentially, the ankle joint permits various oval and rotational motions of the foot and combinations thereof, including inversion, eversion, plantar flexion, dorsiflexion, adduction and abduction. Generally, during active inversion, where the sole of the foot is turned to face medially or inwardly, the motion includes supination, adduction and some degree of plantar flexion. During active eversion, where the sole of the foot is turned laterally or outwardly, the motion includes pronation, abduction and dorsiflexion.

Common ankle injuries include ligament sprains and tears, and in more severe cases, fractures. In athletics, it has been found that over 80 percent of all ankle sprains are inversion injuries, occurring when an athlete runs straight ahead or cuts. The foot may suddenly turn into inversion and plantar flexion and the athlete feels a sharp pain. The mechanism of an ankle sprain involving inversion-plantar flexion usually sprains the anterior talofibular ligament, and if more severe, the calcaneofibular ligament. Occasionally, a fracture of the fibula may occur. Inversion and plantar flexion may also be accompanied by rotation. The mechanism of an eversion sprain involves motion which may tear the deltoid ligament or may produce a fracture off the tip of the medial malleolus.

An excessive dorsiflexion force may jam the talus into the mortise, and may cause a fracture of the talus. Additionally, the Achilles may be injured by the stretching forces of dorsiflexion. Plantar flexion sprains, in their pure form, are rare, inasmuch as there is usually some degree of inversion as well. Ligaments which may be injured include the lateral ligaments, tibiofibular ligaments and others.

Treatment of ankle injuries depends upon the type and severity of damage. Conventional treatment focuses on immobilizing the foot relative to the leg, and may take the form of a cast or brace. It there is excessive swelling, a period of time will be permitted to lapse before application of a cast or brace. In any event, treatment requires that motion of the foot be restricted, particularly inversion and evasion. The immobilization may promote stiffness of the tissues, and that is why rehabilitation is recommended to proceed immediately in all cases of mild-to-moderate ankle sprains and even in some cases of severe but stable sprains. The idea is to allow selected limited motion to avoid reinjury and to promote a more rapid recovery, and to prevent muscular atrophy and stiffness or loss of motion. The essential problem is to stabilize the ankle joint in some manner but permit limited motion to enhance recovery.

Conventional methods of immobilizing an ankle injury involve various forms of taping and in more severe cases, use of ankle braces. Various types of ankle braces or supports have been proposed in the prior art. An example of a pliable-type ankle brace is disclosed in U.S. Pat. No. 3,970,083 where a jacket is fitted around a person's foot and ankle and includes T-shaped stiffened regions on each side. The idea is that a support is provided which may be used for supporting the ankle joint.

An orthotic brace is disclosed in U.S. Pat. No. 4,665,904 which includes a semi-rigid leg-supporting shell for fitting around the lower leg and a semi-rigid foot-supporting shell for conforming to the shape of the foot. The foot-supporting shell is rotatably secured to the leg-supporting shell, thereby resulting in a hinged structure which permits the foot to move in plantar flexion and dorsiflexion.

There are also other types of prior art devices for stabilizing the knee after knee injuries. These devices permit rotation of a knee joint and are shown in examples such as U.S. Pat. Nos. 3,799,158, 4,614,181 and others. These patents, as well as those listed above, do not actually provide a brace which will protect, support and facilitate rehabilitation of an injured ankle joint while permitting the ankle joint to move anatomically within preselected limited ranges.

Accordingly, it is a general object of the present invention to provide an orthotic brace for promoting protection, support/stabilization and rehabilitation of an injured anatomical joint, such as the ankle, by providing a structure which will enable the ankle to move anatomically. The present invention provides an orthotic brace which stabilizes the ankle joint to a preselected degree, i.e., the orthotic brace permits selectively adjustable motion of the foot in dorsiflexion/plantar flexion and inversion/eversion.

Another object of the present invention is to provide an orthotic brace which includes first and second support means for detachably engaging the lower leg and foot, respectively, interconnected by an articulated means which enables the foot to move within a selected range to approximate anatomical motion of the ankle.

Still another object of the present invention is to provide an orthotic brace in which first adjustment means are associated with the articulated means for selectively predetermining the extent of dorsiflexion and plantar flexion. Additionally, second adjustment means are provided with the articulated means for selectively predetermining the extent of inversion and eversion.

These and other objects and advantages of the present invention will be more readily appreciated after a consideration of the attached drawings and the detailed description of the preferred embodiment.

BRIEF DESCRIPTION OF THE DRAWINGS

FIG. 1 is a side view of an individual's right foot, illustrating mounting of the orthotic brace of the present invention on the ankle, and also illustrating the range of motion during dorsiflexion and plantar flexion;

FIG. 2 is an exploded view of the articulated joint of the orthotic brace;

FIG. 2A is a view of an insert for use with the orthotic brace;

FIG. 3 is a view of the side of the orthotic brace corresponding to that adjacent the ankle, and FIG. 3A is a modification;

FIG. 4 is an enlarged, cross-sectional view of a portion or the orthotic brace shown in neutral position;

FIG. 5 is a view, taken from behind an individual's foot, showing the orthotic brace mounted in a neutral position, with the relevant bone structure of the ankle region being shown in dashed outline;

FIG. 6 is a view, similar to that of FIG. 5, showing the movement of the orthotic brace during inversion;

FIG. 7 is a view, similar to FIGS. 5 and 6, showing the orthotic brace when it has moved during eversion; and FIG. 8 is a view showing an orthotic brace according to the present invention adapted for mounting on the knee joint.

DETAILED DESCRIPTION OF THE PREFERRED EMBODIMENT

As mentioned at the outset, it is a principal object of the present invention to provide an orthotic brace which will protect, support and facilitate rehabilitation of an injured anatomical joint. To that end, with reference to an ankle, the orthotic brace of the present invention includes a mechanical joint or articulated means suitably interconnected to the lower leg as well as to the foot, and is selectively adjustable for predetermining the extent or angular range of dorsiflexion/plantar flexion and inversion/eversion of the foot. The orthotic brace is provided with suitable means for enabling a preselected degree of movement of the foot and ankle, to accommodate injuries of varying severity, and to promote a gradually increased range of motion during rehabilitation. The orthotic brace is constructed so that when it is mounted on the lower leg in operable position, it will enable the foot to move in a multi-planar manner. The orthotic brace of the present invention is constructed so that it closely replicates the actual anatomical motion of the foot. That permits normal motion of the foot/ankle which promotes healing.

Construction of the orthotic brace of the present invention can initially be best appreciated from a consideration of FIGS. 1-3. As shown in FIG. 1, an articulated, orthotic brace generally indicated at 10 is mounted on the right foot and lower leg of an individual, and the view is taken from the lateral side. The lower leg is indicated at L, and the foot at F and a shoe or other suitable type of footwear is indicated at S. Orthotic brace 10 is suspended from a first support means such as suspension system 12, detachably engaging the lower portion of leg L. A lower support means such as shell 14, detachably engages the foot, and serves as a cup into which the foot is inserted, prior to insertion into a shoe. While a shoe is shown, it must be appreciated that the orthotic brace of the present invention is not necessarily thought of as requiring a shoe.

Orthotic brace 10 further includes a centrally disposed mechanical joint, which will be referred to as an articulated means 16, interconnected to suspension system 12 and shell 14 by means of a superior arm 18 and an inferior arm 20, respectively. The superior and inferior arms are suitably molded into the suspension system and shell, respectively. With attention now directed to FIG. 2, which is an exploded view of articulated means 16, it can be seen that there is provided a first articular member 22 secured to arm 20 and a second articular member 24 secured to arm 18. The first and second articular members are selectively movable relative to one another of approximate anatomical motion of the ankle as will become hereinafter apparent. First articular member 22 is formed as a semi-spherical member having a first convex outer surface 22a. Second articular member 24 is also formed as a semispherical member having an internal, concave surface 24a as can be seen in FIGS. 4 and 5. As illustrated, ankle brace 10 is mounted on lower leg L and foot F when the ankle is in a neutral position. Returning to FIG. 2, it can be seen that a first bearing surface 26, formed from suitable synthetic material, such as ultra-high molecular weight (UHMW) polyethylene, is provided to nest between first articular member 22 and second articular member 24 when the articulated means is assembled.

It will be noted that first articular member 22 is provided with a circular aperture 22b and first bearing surface 26 and second articular member 24 are provided with elongate, orthogonal apertures 26a and 28, respectively. The articular members are secured together by means of a pin assembly 30, a second bearing surface 32 having an aperture 32a and a cap 34 having a threaded aperture 34a. Pin assembly 30 includes concentric, circular sections 36 and 38 integrally formed on a notched, circular plate 37. Section 38 has a diameter slightly less than that of aperture 22b so that it may rotate therewith when assembled. Pin assembly 30 further includes an offset lug 40 and a pin 42 having external and internal threads. A fastening or lock screw 41 is provided for engaging the internal threads of pin 42 and expanding it so that cap 34 is maintained in proper adjustment, keeping the desired amount of pressure exerted by cap 34 against bearing surface 32, etc. A stop element 43 is secured to first articular member 22 (see FIG. 3 also).

When assembled, as shown in FIG. 4, first and second articular members 22 and 24, respectively, are mounted concentrically, with the convex surface of the first articular member facing the concave surface of the second. Both sandwich therebetween first bearing surface 26, and pin assembly 30 is inserted so that circular section 38 is inserted into circular aperture 22b, with lug 40 being received through aperture 26a to extend through aperture 28 of second articular member 24. Pin 42 extends through aperture 32a of second bearing surface 32, and cap 34 is secured to pin 42.

When articulated means 16 is assembled, such as shown in FIGS. 4 and 5, and mounted on the ankle when in neutral position, pin 42 defines an axis of rotation A alignable generally with the transverse axis of the ankle joint, as shown. As shown in FIGS. 2 and 4, it will be noted that aperture 28 is offset relative to axis of rotation A, i.e., upper end 28a is spaced closer to axis of rotation A than is lower end 28b. The reason for that offset construction is to provide different, preselected angular ranges of motion during inversion and eversion as will be hereinafter explained.

With reference to FIGS. 4 and 5, it will be seen that when foot F is in the neutral position, axis of rotation A is aligned generally with the traverse axis of the ankle joint. In that position, the foot is neither inverted nor everted, nor dorsiflexed nor plantar flexed. The transverse axis of the ankle joint, indicated at A in FIG. 5, extends through the approximate center B of the talus bone. From a practical standpoint, the ankle can be considered to rotate approximately around an axis that passes through center B, and that axis, when the foot is in the neutral position as shown in FIG. 5, is indicated at A. The lateral maleolus is indicated at 50, while the medial maleolus is indicated at 52, with the talus indicated at 54. FIGS. 6 and 7 show action of the foot during inversion and eversion, respectively, and it can be seen that axis of rotation A will incline.

Use of the Orthotic Brace and the Adjustment Means for Predetermining Extent of Anatomical Motion The orthotic brace of the present invention is configured for providing an orthotic device which will protect, support and facilitate rehabilitation of an injured joint, such as an ankle, by enabling a selected, predetermined range of motion which follows the normal movement of the joint, albeit in a limited range. That can be accomplished by the construction which has been just described and with a further explanation of important features of the orthotic brace.

Specifically, as shown in FIG. 1, it can be seen that the orthotic brace can be adjusted to limit the extent of plantar flexion to about 30° away from the neutral position, while dorsiflexion may be limited to about 10°. With the orthotic brace of the present invention, these parameters may be changed, as can be appreciated from a consideration of FIG. 3, and the following description of the first adjustment means for selectively predetermining the extent of relative rotation between the first and second articular members about axis of rotation A.

As shown in FIG. 3 (viewing the orthotic brace from the inside), first articular member 22 is provided with stop element 43 which may be an allen-head screw or the like, or it may be a screw with a wider head (see FIG. 3A). Notched, circular plate 37 with portions or ends 37a and 37b may be thought of as a rotation limit means, inasmuch as either end ultimately will engage stop element 43, depending on whether plantar flexion or dorsiflexion occurs. For example, stop element 43 and end 37a have been set at a position preselected so that the maximum extent of plantar flexion is 30°. That occurs when diagonal arm 20, secured to the foot shell, moves with the foot during plantar flexion (counterclockwise in FIG. 3) so that end 37a engages stop element 43 and is limited with further movement. It will be recalled, with reference to FIG. 2, that lug 40 extends through elongate slot 28 so that it engages sides of that slot, as also can be seen from a consideration of FIG. 2, that lug 40 extends through elongate slot 28 so that it engages sides of that slot, as also can be seen from a consideration of FIG. 4. Thus, pin assembly 30, including plate 37, is rotatable with second articular member 24 and thereby rotates relative to first articular member 22. When dorsiflexion occurs, though a range of motion with a predetermined extent of, for example, 10°, and 37b of plate 37 will ultimately engage stop element 43. Thus, it should be appreciated that by suitably positioning stop element 43, or inserting a different sized stop element (as shown by elongate stop element 43a in FIG. 3A), or increasing or decreasing the length of the notch in plate 37, the angular extent of dorsiflexion and plantar flexion may be selectively predetermined. That is a very important consideration during rehabilitation of a fractured or sprained ankle, as will be described later.

There is also provided a second adjustment means for predetermining the extent of movement of the first and second articular members along an arcuate path defined by aperture 28 which is in effect a track means formed as a slot for suitably receiving lug 40. The arcuate path refers to the extent of preselecting inversion and eversion, and attention is directed to FIG. 2 where it is again noted that lug 40 fits within slot 28 when the ankle brace is assembled. As will be recalled, slot 28 is offset relative to axis of rotation A. This can also be appreciated from a viewing of FIGS. 4 and 5, the latter showing the foot in the neutral position, whereby axis of rotation A of the orthotic brace aligns generally with the transverse axis of the ankle joint. In that neutral position, it will be seen that top 40a of lug 40 is spaced beneath top 28a of elongate slot 28. The bottom 40b of lug 40 is spaced further from bottom 28b of elongate slot 28, meaning that top 28a is offset from axis of rotation A less than bottom 28b. It is to be understood that the radius of curvature of first convex surface 22a is about 1 3/8 inches, roughly, which is approximately one-half of the average ankle width of about 2¾ inches. As will be recalled, motion of the ankle joint is extremely complex, and it is difficult to locate precisely the transverse axis which will be assumed to lie generally along A as shown in FIG. 4. The radius which is that of convex surface 22a extends generally from point B, which is the intersection of the vertical axis C of the ankle joint and transverse axis of rotation A. It must be kept in mind that the radius of convex surface 22a is generally 1 3/8 inches, and it may be more or less as design criteria require for different individuals, and certainly differences for age and sex also being taken into account.

In FIG. 6, the foot is shown inverted 10°–15°, and lug 40 has been displaced along an arcuate path until its bottom has engaged bottom 28b of slot 28. Thus, the axis of rotation A of the orthotic brace now corresponds to the transverse axis of the ankle joint which is inclined or oblique, due to the tendency of the foot to move somewhat in plantar flexion when inversion occurs. Plantar flexion tends to incline the axis of motion of the ankle joint downwardly and medially, while just the opposite occurs during eversion, which is accompanied by dorsiflexion, as shown in FIG. 7.

As illustrated in FIG. 7, the foot has been everted about 5° and top 40a of lug 40 now engages top 28a of slot 28. Because it is generally the case that far less eversion will occur than inversion, it now becomes clear why top 28a of slot 28 is not offset as much from axis of rotation A as is bottom 28b of slot 28. It should be appreciated that dimensioning of slot 28, and offsetting it on second articular member 24 relative to axis of rotation A will predetermine the extent of inversion and eversion.

Use of the orthotic brace of the present invention will now be briefly described with respect to facilitating rehabilitation of a fractured or sprained ankle. Normal movement of a noninjured ankle, measured from a neutral position, is up to about 15° for dorsiflexion and about 40°–50° for plantar flexion. Concerning inversion, a normal extent of motion for an noninjured ankle may be up to 50° while for eversion up to about 20°. After injury to the ankle joint, protective support must be provided, especially in the case of severe injury. Thus, initial treatment may be to use the orthotic brace to immobilize completely the injured ankle. In that case, the orthotic brace would be adjusted so that no ankle joint motion could occur. Ice may be applied to reduce swelling, or it simply may be necessary to wait until swelling diminishes, after which it may be advisable to begin rehabilitation by permitting motion of the ankle joint. Obviously, full degrees of motion should be avoided because reinjury may occur. However, to restrict selectively the extent of motion will enable an individual to exercise the injured ankle through a preselected, limited range. Thus, preselected of the extent of dorsiflexion, plantar flexion, inversion and eversion may be accomplished by suitable positioning of the first and second adjustment means as has been described. Moreover, variations on the extent of motion may be achieved; for example, it may be desired to eliminate eversion entirely, especially in the case of an eversion injury. With eversion curtailed, limited degrees of inversion may be desired and preselecting the extent of motion of dorsiflexion and plantar flexion may also be desired.

FIG. 8 is a view of the orthotic device of the present invention mounted on an injured knee. Also, FIG. 2A illustrates use of an insert 27 which may be keyed into a recess 29 in a different second articular member. Insert 27 is provided with a slot 31 offset differently from axis A so that different ranges of inversion and eversion are permitted.

Thus, the present invention as above-described can be seen to provide an orthotic brace which will not only protect and support an injured ankle, but also may be used in rehabilitation by selectively increasing the extent of a relevant ankle motion. The orthotic brace of the present invention provides multiple planes of motion which closely approximate the normal anatomical motion of the ankle joint. That is in sharp contrast to braces which typically only allow dorsiflexion and plantar flexion. By providing the mating convex and concave surfaces of the ankle brace of the present invention, multiple planar motions may be achieved, thereby enabling an injured ankle to move through its normal anatomical range of motion to facilitate healing.

The first and second articular members can rotate relative to one another, and also move along the arcuate path defined by lug 40 and slot 28. That arcuate path is provided regardless of where the foot is positioned, or is being positioned, in plantar flexion and dorsiflexion. The multiple planar motion of the articulated members can also be appreciated from viewing FIGS. 4–7. As shown in FIGS. 4 and 5, first and second articular members 22 and 24, respectively, can rotate relative to one another (as during plantar flexion or dorsiflexion) about a first plane which is normal relative to axis A. If the foot is inverted 10°–15°, as shown in FIG. 6, then the first and second articular members can rotate relative to one another about another plane normal to axis $A^1$. An infinite number of different, rotational plans between the first and second articular members can be achieved within the overall range defined by the length of slot 28 and its relative offset to axis A (see FIG. 2 again).

There are still further advantages of the orthotic brace of the present invention. For example, it is possible to use the basic multi-planar action on other joints. Or, still considering the ankle joint, it may be possible to place resistance means on the orthotic brace so that resistance exercises can be conducted through the preselected ranges of motion. Assisted forces can be applied to enhance strength in weak muscles.

While the present invention has been shown and described with reference to the foregoing preferred embodiment, it will be appreciated by other skilled in the art that changes in detail and form may be made without departing from the spirit and scope of the invention as defined in the appended claims.

It is claimed and desired to secure by Letters Patent:

1. An articulated, orthotic brace for providing support to an anatomical joint comprising;
    first support means for detachably engaging a body portion adjacent and on one side of the joint;
    second support means for detachably engaging a body portion adjacent and on the opposite side of the joint; and
    articulated means interconnecting the first and second support means including first and second articular members and mounting means mounting the second articular member on the first articular member for relative rotation of the members about an axis extending outwardly from the articular members and this axis occupying a neutral position, the mounting means including a pin extending from one articular member to the other articular member along the axis and including a slot in one articular member through which the pin extends to permit relative displacement of the articular members, the slot defining a guide path along which the pin moves when the articular members are displaced relative to one another, and wherein the relative displacement of the articular members places said axis in a position which is inclined with respect to the position of the axis with the axis in its neutral position.

2. The orthotic brace of claim 1 wherein the first articular member is formed with a convex surface and the second articular member is formed with a concave surface mounted concentrically upon the convex surface of the first articular member.

3. The orthotic brace of claim 2 further including first adjustment means associated with the articulated means for selectively predetermining the extent of relative rotation between the first and second articular members about the axis of rotation.

4. The orthotic brace of claim 3 wherein the first adjustment means includes a limit means movable with the second articular member and rotatable therewith for engaging a stop element mounted on the first articular member.

5. The orthotic brace of claim 4 wherein the limit means includes a notched portion defining ends which alternately engage the stop element.

6. An articulated, orthotic brace for promoting rehabilitation of an injured ankle comprising:
    first support means for detachably engaging the lower leg adjacent the injured ankle;
    second support means for detachably engaging the foot adjacent the injured ankle;
    articulated means interconnecting the first and second support means adjacent one of the ankle's malleoli including first and second articular members and mounting means mounting the second articular member on the first articular member for relative rotation about an axis which extends outwardly to one side of said articulated means and this axis occupying a neutral position, the mounting means including a pin extending from one articular member to the other articular member along the axis and including a slot in one articular member through which the pin extends to permit relative displacement of the articular members, the slot defining a guide path along which the pin moves when the articular members are displaced relative to one another, and wherein the displacement of the second articular member relative to the first articular member swings said axis to a position inclined to the position of the axis with the axis in said neutral position;

first adjustment means associated with the articulated means for selectively predetermining extent of relative rotation of the first and second articular members; and second adjustment means associated with the articulated means for selectively predetermining the extent of relative displacement of the second articular member with respect to the first articular member by selectively predetermining the dimensions of the slot.

7. The orthotic brace of claim 6 wherein the first articular member is formed with a convex surface and the second articular member is formed with a concave surface mounted concentrically upon the convex surface.

8. The orthotic brace of claim 7 wherein the first adjustment means includes a limit means movable with the second articular member as the second articular member rotates relative to the first articular member and a stop element mounted on the first articular member for engaging the limit means.

9. The orthotic brace of claim 8 wherein the limit means includes a notched portion having ends which alternatively engage the stop element.

10. An articulated, orthotic brace for providing support to an anatomical joint comprising:

first support means for detachably engaging a body portion adjacent the joint;

second support means for detachably engaging a body portion on the opposite side of the joint;

articulating means interconnecting the first and second support means, the articulating means including first and second articular members and means interconnecting the articular members to permit selective movement of the articular members relative to one another to approximate anatomical motion;

a pin assembly for securing the articular members to one another, including a pin defining an axis of rotation about which the articular member rotate relative to one another; and a slot in one of the articular members through which the pin defining the axis of rotation extends, the slot forming a track along which the articular members move relative to each other as the pin moves in the slot, the articular members being configured to selectively incline the axis of rotation when the articular members move relative to each other, the range and the degree of inclination of the axis of rotation being predetermined by the dimensions of the slot and the engagement of the pin with the slot.

11. The orthotic brace of claim 10 including rotational limit means on said articulating means for limiting the relative rotational movement between the articular members about the axis of rotation to a predetermined rotational range.

12. The orthotic brace of claim 11 wherein the rotational limit means includes a notched portion on one articular member and a stop member on the other articular member, the notched portion on the one articular member defining ends which alternately engage the stop element on the other articular member.

13. The orthotic brace of claim 10 wherein the slot is elongate and the axis of rotation is inclined over a range limited by the pin engaging the ends of the slot.

14. The orthotic brace of claim 10 in which the configuration of the articular members which selectively inclines the axis of rotation includes a spherically-shaped engagement surface on at least one of the articular member produces arcuate relative movement of the articular members.

15. The orthotic brace of claim 10 in which the pin defining the axis of rotation is fixed relative to one articular member and movable within the slot relative to the other articular member.

16. The orthotic brace of claim 10 including first adjustment means associated with the articulating means for selectively predetermining the extent of relative rotational movement between the articular members about the axis of rotation.

17. The orthotic brace of claim 16 including second adjustment means associated with the articulating means for selectively changing the range over which the axis of rotation is inclined by altering the dimensions of the slot.

18. An articulated, orthotic brace for providing support to an anatomical joint comprising:

first support means for detachably engaging a body portion adjacent the joint;

second support means for detachably engaging a body portion on the opposite side of the joint;

articulating means interconnecting the first and second support means, the articulating means including first and second articular members and means interconnecting the articular members, whereby the articular members are relatively rotatable about an axis of rotation which approximates anatomical motion and also are relatively displaceable with respect to each other to incline the axis of rotation;

said means interconnecting the articular members including a pin extending from one articular member to the other articular member, the pin defining an axis of rotation between the articular members; and a slot in one articular member which said pin extends through, the slot defining an elongate guide path which the pin moves along to change the inclination of the axis of rotation, the range of inclination of the axis of rotation being predetermined by the dimensions of the pin and slot and engagement of the pin with the slot.

* * * * *